(12) United States Patent
Geng et al.

(10) Patent No.: US 11,629,283 B2
(45) Date of Patent: Apr. 18, 2023

(54) N,N,N',N'-TETRADODECYL-SUBSTITUTED DIPHENYL ETHER SULFONATE ANIONIC GEMINI SURFACTANT AND SYNTHESIS METHOD THEREOF

(71) Applicant: PetroChina Company Limited, Beijing (CN)

(72) Inventors: Xiangfei Geng, Beijing (CN); Bin Ding, Beijing (CN); Jianhui Luo, Beijing (CN); Bo Huang, Beijing (CN); Jianyong Xie, Beijing (CN); Pingmei Wang, Beijing (CN); Yang Gao, Beijing (CN); Baoliang Peng, Beijing (CN)

(73) Assignee: PetroChina Company Limited, Beijing (CN)

( * ) Notice: Subject to any disclaimer, the term of this patent is extended or adjusted under 35 U.S.C. 154(b) by 636 days.

(21) Appl. No.: 16/691,969

(22) Filed: Nov. 22, 2019

(65) Prior Publication Data
US 2020/0208045 A1    Jul. 2, 2020

(30) Foreign Application Priority Data
Jan. 2, 2019    (CN) .......................... 201910001658.7

(51) Int. Cl.
    *E21B 43/16*       (2006.01)
    *C09K 8/60*        (2006.01)
                 (Continued)

(52) U.S. Cl.
CPC ............ *C09K 8/604* (2013.01); *C07C 303/06* (2013.01); *C07C 309/49* (2013.01); *C09K 2208/06* (2013.01)

(58) Field of Classification Search
CPC ...... C09K 8/604; C09K 2208/06; E21B 43/16
(Continued)

(56) References Cited

U.S. PATENT DOCUMENTS

| 3,198,736 A | 8/1965 | Henderson |
| 3,775,317 A | 11/1973 | Inami et al. |
| (Continued) |

FOREIGN PATENT DOCUMENTS

| CN | 101104794 A | 1/2008 |
| CN | 101185866 A | 5/2008 |
| (Continued) |

OTHER PUBLICATIONS

Long et al., Synthesis and application in emulsion polymerization of dialkylated diphenyl ether disulfonate, Bai Long et al. Textile Auxiliaries, vol. 35. No.3, Mar. 2018, pp. 16-20.
(Continued)

*Primary Examiner* — William D Hutton, Jr.
*Assistant Examiner* — Ashish K Varma
(74) *Attorney, Agent, or Firm* — Meunier Carlin & Curfman LLC

(57) ABSTRACT

The present invention discloses a N,N,N',N'-tetradodecyl-substituted diphenyl ether sulfonate anionic Gemini surfactant and the synthesis method thereof. It has a structural formula of:

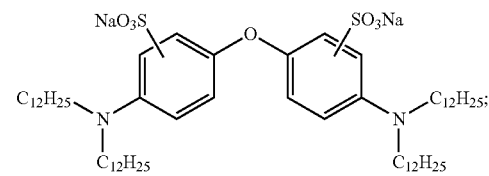

and is prepared in a two-step reaction comprising: S1. subjecting 4,4'-diaminodiphenyl ether and bromododecane to an amine alkylation reaction to obtain N,N,N', N'-tetradodecyl-substituted diphenyl ether; and S2.
(Continued)

sulfonating the N,N,N',N'-tetradodecyl-substituted diphenyl ether with concentrated sulfuric acid to produce the target product, N,N,N',N'-tetradodecyl-substituted diphenyl ether sulfonate. The surfactant of the present invention has a high surface activity and can be synthesized with a simple procedure under mild reaction conditions, and can be easily separated and purified. The surfactant of the present invention is promising in applications for alkaline/surfactant in tertiary oil recovery, for polymer/surfactant binary compound flooding, alkaline/surfactant/polymer tertiary compound flooding, microemulsion emulsifier, and the like, and may also be compounded with common surfactants to lower the cost, thereby enabling its application in a large scale.

1 Claim, 3 Drawing Sheets

(51) Int. Cl.
  *C07C 303/06* (2006.01)
  *C07C 309/49* (2006.01)
(58) Field of Classification Search
  USPC .................................................. 166/270.1
  See application file for complete search history.

(56) References Cited

U.S. PATENT DOCUMENTS

| | | | |
|---|---|---|---|
| 5,352,573 | A | 10/1994 | Seto et al. |
| 11,097,239 | B2 * | 8/2021 | Ding ............... C09K 8/584 |
| 2004/0156994 | A1 | 8/2004 | Wiese et al. |
| 2010/0029880 | A1 * | 2/2010 | Zhang ............... C09K 8/584 |
| | | | 526/287 |
| 2017/0321111 | A1 * | 11/2017 | Velez ............... C09K 8/584 |
| 2017/0369759 | A1 * | 12/2017 | Nguyen ............... C09K 8/80 |
| 2019/0055459 | A1 | 2/2019 | Zelenev et al. |
| 2019/0154404 | A1 | 5/2019 | LeMarbe et al. |
| 2020/0208045 | A1 | 7/2020 | Geng et al. |

FOREIGN PATENT DOCUMENTS

| | | |
|---|---|---|
| CN | 102380330 A | 3/2012 |
| CN | 102614805 A | 8/2012 |
| CN | 102806047 | 12/2012 |
| CN | 102993413 | 3/2013 |
| CN | 103173198 | 6/2013 |
| CN | 103864648 A | 6/2014 |
| CN | 104263341 | 1/2015 |
| CN | 104830301 | 8/2015 |
| CN | 105435706 A | 3/2016 |
| CN | 106590570 | 4/2017 |
| CN | 106590578 | 4/2017 |
| CN | 107304162 | 10/2017 |
| CN | 109851530 A | 6/2019 |
| JP | H05194788 | 8/1993 |
| JP | 2003301109 A | 10/2003 |
| WO | 2010148177 A2 | 12/2010 |
| WO | 2016176385 | 11/2016 |

OTHER PUBLICATIONS

Zhou et al. Synthesis and Characterization of a Type of Gemini Surfactant, Zhou Xuan et al. Guangzhou Chemical Industry, vol. 41, No. 4, Feb. 2013, pp. 90-92.
Chinese search report, dated Nov. 15, 2018. 8 pages.
C.A.Bunton, L.Robinson. Catalysis of nucleophile substitutions by micelles of dicationic detergents [J]. F. J. Org. Chem, 1971(36): 2346-2352.
Y.P.Zhu, A. Masuyama, Deinega, Preparation and properties of double-or-triple-chain surfactants with two sulfonate groups derived from N-acyldiethanolamines [J]. J. Am. Oil Chem. Soc, 1991(68): 539-543.
Zhu Y P, Masuyama A, Okahara M. Preparation and surface active properties of amphipathic compounds with two sulfate groups and two lipophilic alkyl chains [J] J Am Oil Chem Soc,1990, 67(7): 459-463.
Zhu. Y P, Masuyama A, Kirito M. Preparation and surface-active properties of new amphipathic compounds with two phosphate groups and two long-chain alkyl groups [J] J Am Oil Chem Soc, 1991, 68(4): 268-271.
Menger F M,Littau CA. Gemini surfactants: synthesis and properties[J]. J. Am Chem Soc, 1991(113): 1451-1452.
Rosen, MJ. Geminis: A new Generation of surfactants. [J] J Chem Technol, 1993(30): 23-33.
Zana R,Talmon Y. Dependence of aggregate morphology on structure of dimeric surfactants. [J] Nature, 1993(362): 228-229.
Ding Bin et al. "Characteristics and EOR mechanisms of nanofluids Permeation flooding for tight oil"; Petroleum Exploration and Development, vol. 47, No. 4; 10 pages.
Ding Shan et al.; Characteristics and EOR mechanism of nanofluids permeation flooding for tight oil, Petroleum Exploration and Development, vol. 47, No. 4; 9 pages.
Hu Jian-Ii et al, "Synthesis and Surface Activities of Sodium Oleoyl Amido Diphenyl Ether Disulfonate", Fine Chemicals, vol. 22, No. 5.
M.E.Ginn, et al, "Performance Evaluation of selected Fabric Softeners", The Journal of the American Oil Chemists Society, vol. 42; 5 pages.
M. Ben Moshe et al; "Structure of microemulsions with gemini surfactant"; Studied by solvatochromic probe and diffusion NMR, Journal of Colloid and Interface Science,vol. 276, No. 1; 6 pages.
Cheng Yu—qiao et al.; "Synthesis and surface active properties of a bis-sodium lauryl phenyl ether sulfonate gemini surfactant"; China Surfactant Detergent & Cosmetics, vol. 41, No. 5; 5 pages.
Tiliu Jiao et al.; "Synthesis and Properties of Dioctyl Diphenyl Ether Disulfonate Gemini Surfactant", Physical Chemistry, vol. 53, No. 4; 6 pages.
J.A.Goodson et al; "The Chemotherapy of Amoebiasis Part III. Variants of Bis(Diamylamino)Decane", Brit.J.Pharmacol, vol. 62, No. 3; 10 pages.
Office Action and its English Translation issued in CN Application No. 201910001672.7; dated Oct. 23, 2020; 6 pages.
Search Report and its English Translation issued in CN Application No. 201910001672.7; dated Oct. 15, 2020; 9 pages.
Xiaoyan, Liu. The synthesis and application of sulfonate Gemini Surfactants, Nanjing University of Science & Technology M.D. Dissertation.
Wu et al. Research on Sulfonate Gemini Surfactant Ultralow Interfacial Tension Foam Systems, Advances in Fine Petrochemicals, vol. 18, No. 4.
STN Structural retrieval.
Jing Xiao Ming; "Synthesis and Properties of SodiumAlkyl Dibenzene Sulfonate Type Double Anionic Surfactant" China Excellent Master's Thesis Engineering Science and Technology Series 1, No. 12, Dec. 15, 2013; 90 pages.
Zhao Rui-xue et al., "Synthesis and Surface Activities of the thylene Glycol Diphenyl Ether Disulfonate Gemini Surfactants Contained Two Carbonyl Group"; Journal of Jilin Institute of Chemical Technology, vol. 31, No. 5, May 31, 2014; May 2014; 6 pages.
Xiaoyan, Liu, "The synthesis and application of sulfonate Gemini surfactants", China Excellent Master's Thesis Engineering Science and Technology Series 1, No. 1, Jan. 15, 2016; Mar. 2015, 82 pages.
Bai Long et al.; "Performance of mono- and di-dodecyl diphenyl ether disulfonate"; Textile Auxiliaries,vol. 35, No. 8,Aug. 31, 2018; Aug. 2018; 5 pages.
Office Action and Search Report issued in counterpart CN Application No. 20190001658.7; dated Dec. 25, 2020; 12 pages.

* cited by examiner

N,N,N',N'-TETRADODECYL-SUBSTITUTED DIPHENYL ETHER SULFONATE ANIONIC GEMINI SURFACTANT AND SYNTHESIS METHOD THEREOF

CROSS-REFERENCE TO RELATED APPLICATION

This application claims priority to Chinese Patent Application No. 201910001658.7, filed on Jan. 2, 2019, which is hereby incorporated by reference in its entirety.

TECHNICAL FIELD

Embodiments of the present invention relate to the field of surfactants, and specifically to a N,N,N',N'-tetradodecyl-substituted diphenyl ether sulfonate anionic Gemini surfactant and synthesis method thereof.

BACKGROUND ART

In 1971, Bunton et al. conducted a study on the surface activity of alkylene-bis(alkyldimethylammonium bromide) [$C_mH_{2m+1}N^+(CH_3)_2$—$(CH_2)_5$—$C_mH_{2m+1}N^+(CH_3)_2$]$Br^-_2$, in which the properties of such surfactants were investigated when the linking group is a hydrophilic, hydrophobic, flexible, or rigid group (C. A. Bunton, L. Robinson. Catalysis of nucleophilic substitutions by micelles of dicationic detergents [J]. F. J. Org. Chem, 1971 (36): 2346-2352). In 1974, Deinega et al. synthesized a series of new amphiphilic molecules having a molecular structure of a long hydrocarbon chain, an ionic head group, a linking group, a second ionic head group, and a second hydrocarbon chain in the order (Y. P. Zhu, A. Masuyama, Deinega, Preparation and properties of double-or-triple-chain surfactants with two sulfonate groups devised from N-acyldiethanolamines [J]. J. Am. Oil Chem. Soc, 1991 (68): 539-543). In early 1990s, Okahara et al. from Osaka University in Japan synthesized a number of anionic Gemini surfactants by using a flexible group as a linker and investigated their properties (Zhu Y P, Masuyama A, Okahara M. Preparation and surface active properties of amphipathic compounds with two sulfate groups and two lipophilic alkyl chains [J] J Am Oil Chem Soc, 1990, 67 (7): 459-463; Zhu. Y P, Masuyama A, Kirito M. Preparation and surface-active properties of new amphipathic compounds with two phosphate groups and two long-chain alkyl groups [J] J Am Oil Chem Soc, 1991, 68 (4): 268-271; Zhu Y. P, Masuyama A, Kiriito Y. Preparation and properties of double or triple-chain surfactants with two sulfonate groups derived from N-acyldiethanolamines [J] J Am Oil Chem Soc, 1991, 68 (7) 539-543). However, systematic and intentional research on these novel surfactants had not been started until 1991 when Menger and Littau from Emory University synthesized and studied a double-alkyl-chain surfactant having a rigid group as a linker, which was named "Gemini" surfactant (from the constellation Gemini in Astronomy) (Menger F M, Littau C A. Gemini surfactants: synthesis and properties[J]. J. Am Chem Soc, 1991 (113): 1451-1452). Both the Rosen group and the Zana group acknowledged this nomenclature and conducted numerous focused studies (Rosen, M J. Geminis: A new Generation of surfactants. [J] J Chem Technol, 1993(30): 23-33; Zana R, Talmon Y. Dependence of aggregate morphology on structure of dimeric surfactants. [J] Nature, 1993 (362): 228-229). As the structural features, superior performance, and structure-effect relationship of Gemini surfactants were further discovered, this new type of surfactants have attracted particular interest from scientists worldwide and drawn general attention from the industries, and efforts have been made to find their applications.

A Gemini surfactant has a structure in which two surfactant molecules are linked together via a chemical bond, such a structure effectively overcomes the electrostatic repulsive force between charges of the ionic head groups of the same polarity and overcomes the repulsion from the hydrated layer of the head group, and facilitates compact alignment of the surfactant ions. As compared to common surfactants, Gemini surfactants have very high surface activity in that (1) they tend to tightly align on a gas/liquid interface, thereby effectively reducing the surface tension of water; (2) they easily aggregate to form micelles and have an extremely low critical micelle concentration, and the low critical micelle concentration (the cmc value) indicates better solubility of Gemini surfactants than conventional surfactants; (3) they form irregular micelles at a low concentration, rendering the aqueous solution with special phase behavior and rheology, which are particularly useful in engineering; (4) they have a very low Krafft point, allowing a low working temperature; (5) they can produce a substantial synergistic effect in combination with a common surfactant; (6) they have a good ability of dispersing calcium soap; and (7) they have an excellent wetting performance.

Studies on Gemini surfactants started relatively late in China. Although there is a list of diverse products available nowadays, their development, research of their performance, and their application are still falling behind foreign countries, especially in finding raw materials having an intrinsic symmetric structure that may be used in synthesis of Gemini surfactants having better performances.

SUMMARY OF THE INVENTION

An objective of the present invention is to provide a N,N,N',N'-tetradodecyl-substituted diphenyl ether sulfonate anionic Gemini surfactant and the synthesis thereof. The surfactant according to the present invention has a high surface activity, can be synthesized by a simple method under mild reaction conditions, and can be easily separated and purified. The surfactant according to the present invention is promising in applications for alkaline/surfactant in tertiary oil recovery, for polymer/surfactant binary compound flooding, alkaline/surfactant/polymer tertiary compound flooding, microemulsion emulsifier, and the like, and may also be compounded with common surfactants to lower the cost, thereby opening a window for its large-scale application.

In one aspect, an embodiment of the present invention provides a novel anionic Gemini surfactant, more particularly the N,N,N',N'-tetradodecyl-substituted diphenyl ether sulfonate anionic Gemini surfactant, having the structural formula of:

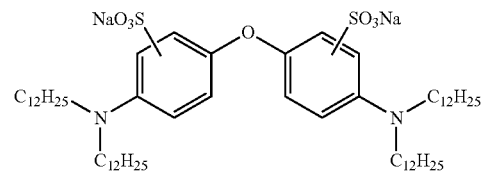

In another aspect, an embodiment of the present invention provides a method for synthesis of the above anionic Gemini surfactant, comprising:

S1. subjecting 4,4'-diaminodiphenyl ether and bromododecane to an amine alkylation reaction to obtain N,N,N',N'-tetradodecyl-substituted diphenyl ether;

S2. sulfonating the N,N,N',N'-tetradodecyl-substituted diphenyl ether with concentrated sulfuric acid to produce the target product, N,N,N',N'-tetradodecyl-substituted diphenyl ether sulfonate.

The surfactant according to the present invention has a high surface activity, can be synthesized by a simple method under mild reaction conditions, and can be easily separated and purified. 4,4'-diaminodiphenyl ether is first reacted with bromododecane to carry out an amine alkylation reaction, in which the amino groups in 4,4'-diaminodiphenyl ether are alkylated to obtain N,N,N',N'-tetradodecyl-substituted diphenyl ether. Then N,N,N',N'-tetradodecyl-substituted diphenyl ether is sulfonated with sulfuric acid to eventually obtain a sulfonate, i.e., the target product. The reaction in the second step is an acid-base reaction carried out in an aqueous phase, followed by a very simple post-treatment, which allows for mass production.

The above synthesis steps will be described hereinafter in more details.

The route of synthesis according to the present invention is shown below:

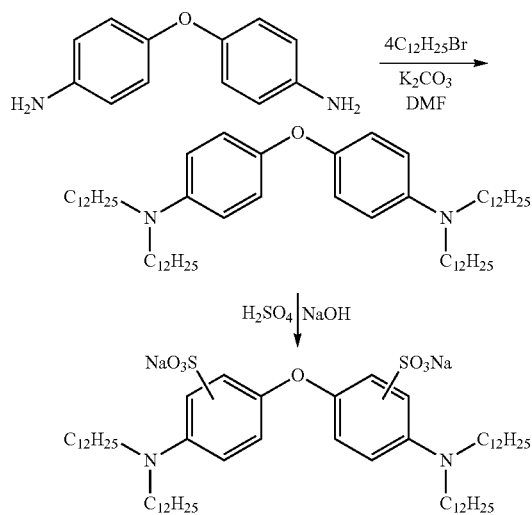

S1. Subjecting 4,4'-diaminodiphenyl ether and bromododecane to an amine alkylation reaction to obtain N,N,N',N'-tetradodecyl-substituted diphenyl ether.

Preferably, the alkylation reaction is conducted in an atmosphere of a protective gas. More preferably, the protective gas includes nitrogen and inert gases.

Preferably, the amount of bromododecane charged is preferably more than 4 times of the equivalent amount of 4,4'-diaminodiphenyl ether, in order to ensure the alkylation of amino groups to be as complete as possible. In a preferred embodiment of the present invention, the molar ratio of 4,4'-diaminodiphenyl ether to bromododecane is 1: (4.1-4.4).

Preferably, in the alkylation reaction, N,N-dimethyl formamide (DMF) is used as a solvent, and $K_2CO_3$ is used as an acid binding agent to keep the system at a pH of 7-10.

Preferably, the content of $K_2CO_3$ added in the system is 20 wt %.

More preferably, the alkylation reaction is carried out at 60 to 70° C.; and after the reaction is complete, post-treatment purification is conducted to obtain N,N,N',N'-tetradodecyl-substituted diphenyl ether.

In a preferred embodiment of the present invention, the post-treatment purification comprises: adding water to allow partitioning, extracting with an organic extracting agent, concentrating the organic phase until dryness, purifying by column chromatography, and drying, to obtain an intermediate product N,N,N',N'-tetradodecyl-substituted diphenyl ether.

As the organic extracting agent, conventional organic solvents such as ethyl acetate, dichloromethane, and chloroform can be chosen. Preferably, the organic extracting agent is ethyl acetate. The detailed extraction procedure comprises: extracting the aqueous phase three times with ethyl acetate, combining the organic phases, washing the combined organic phase once with water, and separating and concentrating the organic phase until dryness.

Preferably, the developing solvent for the column chromatographic purification is a system of petroleum ether and ethyl acetate. More preferably, V (petroleum ether):V (ethyl acetate)=10:1.

S2. sulfonating the N,N,N',N'-tetradodecyl-substituted diphenyl ether with concentrated sulfuric acid to produce the target product, N,N,N',N'-tetradodecyl-substituted diphenyl ether sulfonate.

Preferably, step S2 comprises: adding N,N,N',N'-tetradodecyl-substituted diphenyl ether to a solvent, adding concentrated sulfuric acid dropwise thereto to carry out reaction; after the reaction is complete, quenching the system by adding water, separating the aqueous phase in which the intermediate product of the reaction is dissolved, adding NaOH to the aqueous phase to adjust the pH to a basic pH, and concentrating the aqueous phase until dryness, to obtain the target product N,N,N',N'-tetradodecyl-substituted diphenyl ether sulfonate.

Preferably, the solvent is acetic acid.

More preferably, after separating the aqueous phase, the method further comprises extracting the aqueous phase with an extracting agent, separating the aqueous phase and concentrating it until dryness, and purifying it by column chromatography, so as to obtain the intermediate product; dissolving the intermediate product in water and then adding NaOH to adjust the pH to a basic pH.

As the organic extracting agent, conventional organic solvents such as ethyl acetate, dichloromethane, and chloroform can be chosen. Preferably, the organic extracting agent is ethyl acetate. The detailed extraction procedure comprises: extracting the aqueous phase three times with ethyl acetate, combining the organic phases, washing the combined organic phase once with water, and separating and concentrating the aqueous phase until dryness.

Preferably, during the dropwise addition of concentrated sulfuric acid, due to the drastic exothermic reaction, it is necessary to place the reaction system in an ice water bath, and after completion of the dropwise addition, warm it to room temperature to carry out reaction.

Preferably, NaOH is added to adjust the pH to 10.

Preferably, the NaOH is a 1 mol/L NaOH aqueous solution.

In the synthesis method according to the present invention, the end point of reaction is always monitored by TLC.

In comparison with the prior art, the present invention is advantageous in that:

a novel surfactant, the N,N,N',N'-tetradodecyl-substituted diphenyl ether sulfonate anionic Gemini surfactant, is provided, which has not yet been reported as a target product in the literature;

the method for synthesis according to the present invention is simple, its synthesis procedure is composed of a step of amine alkylation and a step of sulfonation, with mild reaction conditions and easy operation, and the product can be easily separated and purified;

the target product of the present invention has superior surface activity, with a critical micelle concentration (cmc) of 0.016 wt %, which is lower than that of the anionic surfactant sodium dodecyl sulfonate (cmc=0.28 wt %) by one order of magnitude, and lower than that of the cationic surfactant dodecyl trimethylammonium bromide (cmc=0.42 wt %) by one order of magnitude. Its surface tension at the critical micelle concentration is 23 mN/m, which is lower than that of sodium dodecyl sulfonate ($\gamma_{cmc}$=39 mN/m) by 16 mN/m, and lower than that of dodecyl trimethylammonium bromide ($\gamma_{cmc}$=40 mN/m) by 17 mN/m.

DETAILED DESCRIPTION OF THE INVENTION

The present invention will be further illustrated with reference to preferred examples in order to provide a clearer explanation of the present invention. The detailed description provided hereinafter is merely illustrative and not limiting, which is not to be construed as limitation to the scope of protection of the present invention.

Preparation of N,N,N',N'-tetradodecyl-Substituted diphenyl ether sulfonate

(1) Synthesis of N,N,N',N'-tetradodecyl-Substituted diphenyl ether

To a three-neck flask equipped with a stirring device and placed in a water bath at a constant temperature, 25.00 g (124.85 mmol) 4,4'-diamino diphenyl ether, 10.46 g (41.95 mmol) bromododecane, and 5.80 g $K_2CO_3$ (20 wt %) as an acid-binding agent were sequentially added. The system pH was kept at 7-10, and 150 mL DMF as a solvent was added under nitrogen protection. The system was stirred and warmed to 60° C., and a reaction was allowed to proceed for 24 h before it was completed (the reaction end point was monitored by TLC, using a developer of V (petroleum ether):V (ethyl acetate)=10:1). Water was added to allow partitioning. The aqueous phase was extracted three times with ethyl acetate, and the organic phase was washed once with water, concentrated until dryness, purified through a column, and dried to give 80 g (91.58 mmol) of a yellow oily intermediate product, N,N,N',N'-tetradodecyl-substituted diphenyl ether.

(2) Synthesis of N,N,N',N'-tetradodecyl-Substituted diphenyl ether sulfonate In the same reaction apparatus as in (1), 2.00 g (9.158 mmol) N,N,N',N'-tetradodecyl-substituted diphenyl ether and 50 mL acetic acid as a solvent were sequentially added to a three-neck flask, to which 10 mL concentrated sulfuric acid was added dropwise under stirring on an ice bath. Upon completion of the dropwise addition, the temperature was raised to room temperature, and a reaction was carried out for 6 h (the reaction end point was monitored by TLC). After the reaction was completed, the mixture was quenched by water and partitioned. The aqueous phase was extracted three times with ethyl acetate, and the organic phase was washed once with water, concentrated until dryness, and purified through a column. The product was dissolved in water, to which a 1 mol/L NaOH aqueous solution was slowly added dropwise until the system pH was adjusted to 10, and the aqueous phase was collected and concentrated until dryness, to obtain 1.8 g (1.75 mmol) of a brown viscous product, N,N,N',N'-tetradodecyl-substituted diphenyl ether sulfonate.

IR Spectrum of N,N,N',N'-tetradodecyl-Substituted diphenyl ether sulfonate

Figure 1:
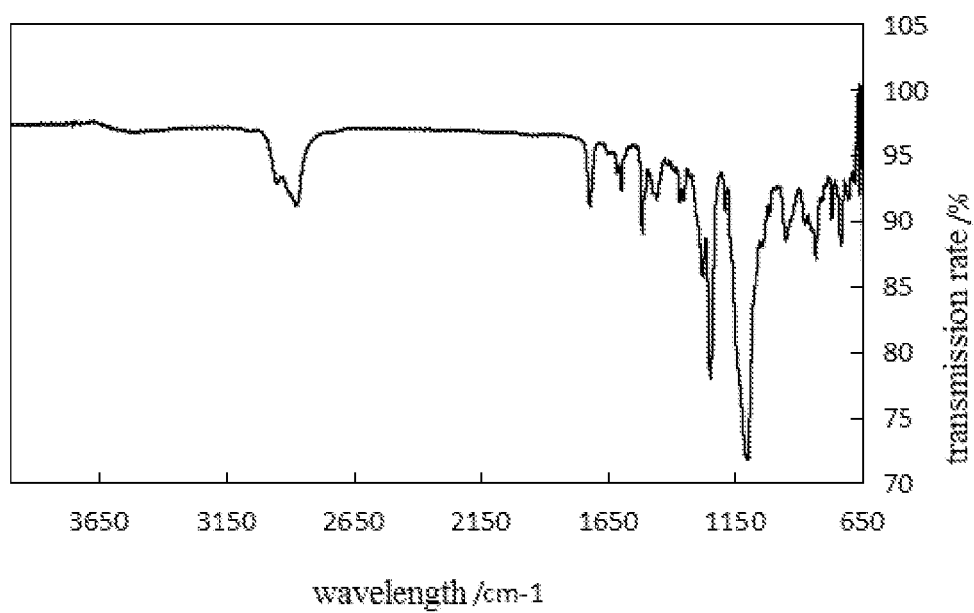
FIG. 1 is the IR spectrum of the target product of the present invention, N,N,N',N'-tetradodecyl-substituted diphenyl ether sulfonate.

The IR spectrum of the target product is shown in FIG. 1, from which it can be seen that:

2946, 2869 are stretching vibration peaks of $CH_3$, $CH_2$; 1610, 1591, 1507, 1450 are vibration peaks of the benzene-ring core; 873, 828 are characteristic peaks of p-substitutions on the benzene ring; 1274, 1241 are C—N stretching vibration peaks; 1100, 1049 are C—O stretching vibration peaks; 1091 is the S=O stretching vibration peak; 719 is the $(CH_2)_n$ (n≥4) in-plane wagging vibration peak; and 622 is the S—O stretching vibration peak.

Figure 2:
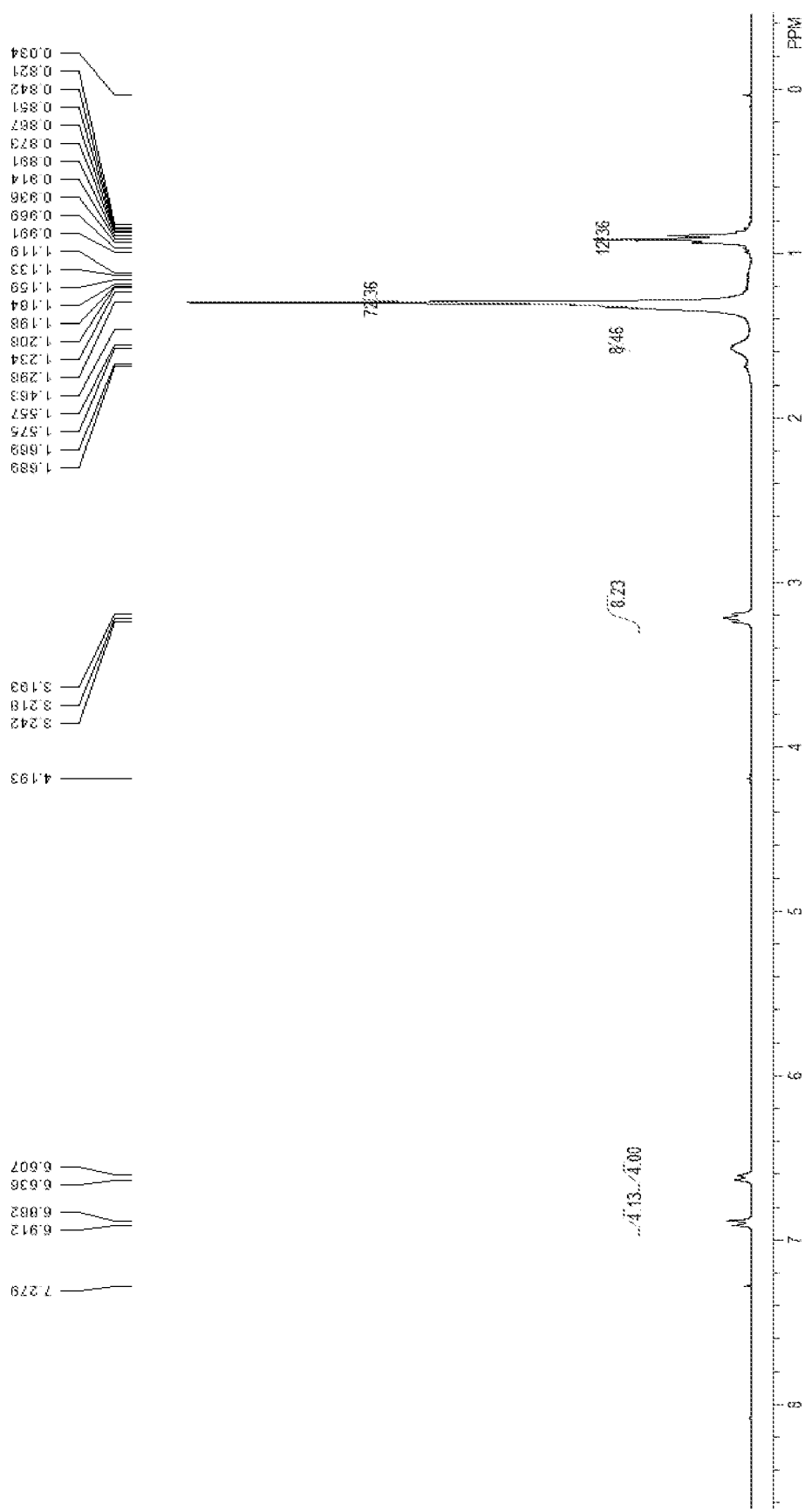
FIG. 2 is the $^1$H NMR spectrum of the target product of the present invention, N,N,N',N'-tetradodecyl-substituted diphenyl ether sulfonate.

$^1$H-NMR Spectrum of N,N,N',N'-tetradodecyl-Substituted diphenyl ether sulfonate The $^1$H-NMR spectrum of the target product is shown in FIG. 2, from which it can be seen that:

$^1$H-NMR (400 MHz, $CDCl_3$): δ: 0.82-0.99 [3H, $CH_3CH_2$], 1.12-1.29 [16H, $CH_3(CH_2)_8CH_2CH_2$], 1.46-1.69 [2H, $(CH_2)_{10}CH_2CH_2N$], 3.19-3.24 [2H, $(CH_2)_{10}CH_2CH_2N$], 6.60-6.64 [1H, NCCH], 6.88-6.91 [1H, OCCH].

Figure 3:
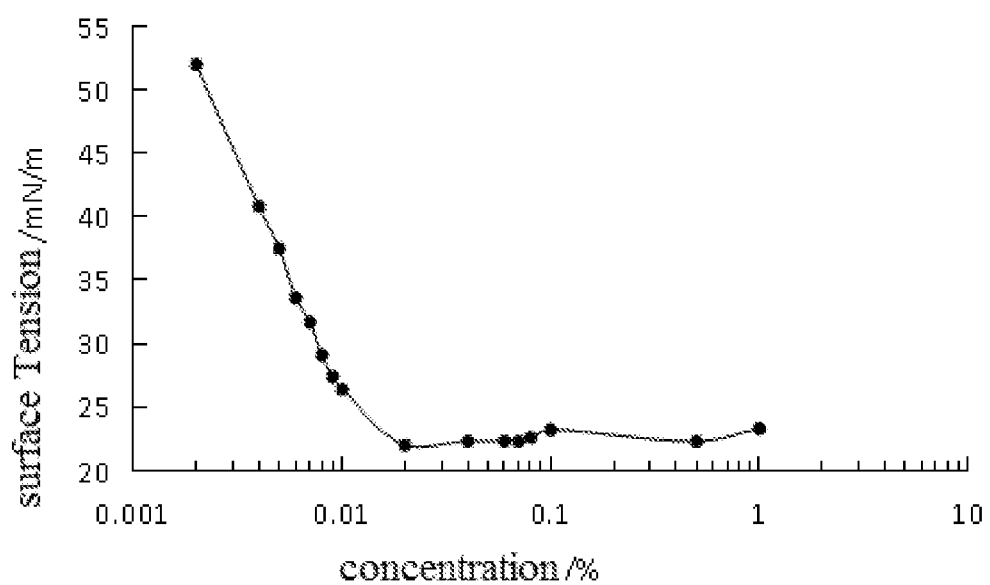
FIG. 3 is a surface tension-concentration diagram (at 25° C.) of the target product of the present invention, N,N,N',N'-tetradodecyl-substituted diphenyl ether sulfonate.

Obviously, the above examples of the present invention are merely exemplified for the purpose of clearly illustrating the present invention, and the embodiments of the present invention are not limited thereto. For those skilled in the art, various modifications or alterations can be made on the basis of the above description, and any obvious modifications or alterations as extension of the technical solutions of the present invention are also intended to be included within the scope of protection of the present invention.
What is claimed is:
1. A N,N,N',N'-tetradodecyl-substituted diphenyl ether sulfonate anionic Gemini surfactant, having the structural formula:
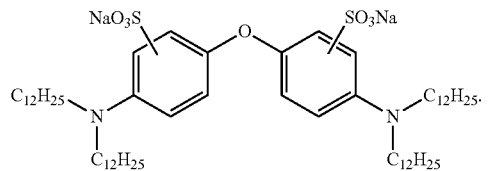

Surface Activity of N,N,N',N'-tetradodecyl-Substituted diphenyl ether sulfonate The ability of a surfactant to lower the surface tension of water is an important parameter for evaluation of its surface activity. The surface tension of aqueous solutions of the target product at different concentrations at 25° C. was measured by the hanging plate method, and a curve of the concentration-dependent surface tension of aqueous solution of the N,N,N',N'-tetradodecyl-substituted diphenyl ether sulfonate Gemini surfactant was plotted (FIG. 3). The surface activity parameter of this Gemini surfactant can be calculated from this curve: a critical micelle concentration (cmc) of 0.016 wt %, and surface tension at cmc ($\gamma_{cmc}$) of 23 mN/m.